United States Patent [19]

Miyano

[11] 4,002,663
[45] Jan. 11, 1977

[54] DEUTERATED PROSTAGLANDIN ANALOGS

[75] Inventor: Masateru Miyano, Northbrook, Ill.

[73] Assignee: G. D. Searle & Co., Chicago, Ill.

[22] Filed: Mar. 3, 1975

[21] Appl. No.: 554,965

[52] U.S. Cl. .................. 260/468 D; 260/345.7; 260/448.8 R; 260/514 D; 424/305; 424/317
[51] Int. Cl.² .................................. C07C 177/00
[58] Field of Search .................. 260/468 D, 514 D

[56] References Cited
UNITED STATES PATENTS 3,903,143  9/1975  Mueller .......................... 260/514

OTHER PUBLICATIONS

Hamberg et al., J.B.C., 246, 1073 (1971).

*Primary Examiner*—Robert Gerstl
*Attorney, Agent, or Firm*—Barbara L. Cowley; Michael T. Murphy

[57] ABSTRACT

Deuterated analogs of prostaglandins have been prepared and found to display increased activity as antifertility, bronchodilator and/or bronchoconstrictor agents compared to the natural prostaglandins. The analogs are conveniently prepared by reduction of the 15-keto group and/or the 9-keto group with a deuterated reducing agent.

3 Claims, No Drawings

DEUTERATED PROSTAGLANDIN ANALOGS

The present invention is concerned with novel chemical compounds represented by the following structural formula

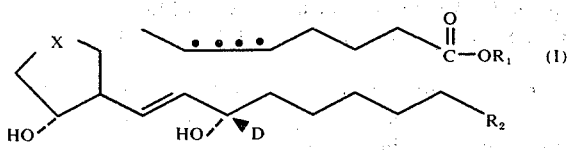

wherein X is a radical selected from the group consisting of keto, α-hydroxymethylene, β-deuterio-α-hydroxymethylene and β-hydroxymethylene, $R_1$ is hydrogen or a lower alkyl radical, $R_2$ is hydrogen or a methyl radical, and the dotted line indicates the presence of an optional 5,6-double bond.

The lower alkyl radical contains 1–6 carbon atoms and is typified by methyl, ethyl, propyl, butyl, pentyl, hexyl, and the corresponding branched chain isomers thereof.

Especially preferred compounds of the present invention are those of the formula

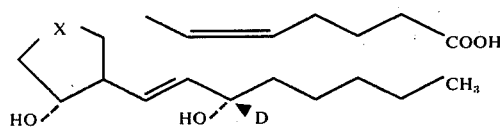

wherein X is keto, α-hydroxymethylene, β-hydroxymethylene or β-deuterio-α-hydroxymethylene.

The compounds of this invention are useful in view of their increased pharmacological activity over their natural analogs.

The compounds of the present invention show utility as anti-hypertensive, antithrombogenic, antifertility, antiulcer and bronchodilator or bronchoconstrictor agents.

The anti-fertility activity of the instant compounds is illustrated by the following assay:

Sexually mature female Syrian golden hamsters (9–10 weeks old) are caged with males. Vaginal smears are taken daily at the same time each day by means of a pipette. The presence of sperm is considered positive evidence of insemination and the day of insemination is designated as day 1 of pregnancy. Pregnant females are then injected daily with test compound beginning on day 1 through day 5. The route of administration may be either subcutaneous or intragastric. The daily injection is usually in a volume of 0.2 ml. corn oil. However, the volume and vehicle may vary depending on the physical characteristics of the particular compound being tested. All animals are sacrificed with dry ice ($CO_2$) on the morning of day six. The entire reproductive tract is removed and the uterus and ovaries trimmed of extraneous tissue. The total number of implantation sites is counted and recorded. By observation, day six size sites are designated as normal and any sites which are smaller and/or pale or resorbing are designated as abnormal. The total number of corpora lutea are counted and recorded. Again, by observation, the red corpora are considered normal and the pale, pink or white regressed corpora are considered abnormal.

A single dose of compound is classified as active or inactive on the basis of the per cent implantation, which is derived by dividing the total number of implantation sites by the total number of corpora lutea and multiplying by 100. A test compound with a 50% or less implantation rate is considered active. A test compound with a 51% or more implantation rate is considered inactive. Abnormal implantation sites and corpora lutea are also reported when 20% or more sites are abnormal, or, if no abnormal sites, only 50% or more abnormal corpora lutea. The $ED_{50}$ of a compound is approximated from inspection or calculated according to the method of Berkson (*J. Amer. Stat. Assoc.*, 48, (263): 565,1953). Estrone is employed as the standard.

When tested in the above procedure, 9β,15β-bisdeuterio-9α,11α,15α-trihydroxy-5-cis,13-trans-prostadienoic acid was found to be active and more potent than its natural analog.

The bronchoconstricting activity of the instant compounds is illustrated by the following assay:

Male, Hartley guinea pigs weighing approximately 300 grams are anesthetized with pentobarbital sodium. A tight-fitting trochar is inserted into the trachea down to the level of the bronchial bifurcation. The trochar is connected to a small animal respirator and a saline-filled cannula terminating in the trochar leads to a pressure transducer. Changes in trachael pressure are recorded on a polygraph. The animals are β-blocked with propranolol.

Compounds to be tested are administered intravenously or intragastrically at various times prior to the intravenous administration of the bronchoconstricting agent, $PGF_{2\alpha}$. Activity is expressed in terms of the percentage inhibition of $PGF_{2\alpha}$-induced bronchoconstriction. Four animals per group are utilized. A mean of 50% inhibition is required to be considered significant.

When tested in the above procedure, 15β-deuterio9β,11α,15α-trihydroxy-5-cis,13-trans-prostadienoic acid was found to be more active as a bronchodilator than natural $PGF_{2\beta}$. Testing of 9β,15β-bisdeuterio-9α,11α,15α-trihydroxy-5-cis, 13-trans-prostadienoic acid showed approximately a threefold increase in activity as a bronchoconstrictor over the natural analog, $PGF_2\alpha$.

Additionally, the smooth muscle stimulating activity of the instant compounds is determined by the following assay:

Activity of the test compound on isolated segments of ascending colon from gerbils is determined using a modification of the method of Weeks, Schultz, and Brown, [*J. Appl. Physiol.*, 25, 783–5 (1968)]. The ascending colon is removed from 80–120 gram, mature, male *Meriones unguiculatus* and mounted in 2 ml. of de Jalon's solution as described by Ambache et al. [*J. Phsiol., London*, 176, 378–408, (1965)]. The bath is maintained at 30°C., gassed with $O_2$, and suspended. Contractions are measured with a Narco Biosystems isotonic transducer and recorded on a Narco Biosystems physiograph. Two four-point parallel line bioassays are conducted on separate segments of tissue, using two concentrations of test compound and two concentrations of the standard, $PGF_{2\alpha}$. The bath is rinsed with a de Jalon solution after each contraction of the tissue. The test compound or standard is added to the bath at four minute intervals in a Latin square design. The amplitudes of the muscle contractions are measured on the recorder paper and used to determine the potency of the test compound relative to the standard by the method of Finney [*Statistical Method in Biological Assay*, 2nd ed. (1964)].

When tested in the above procedure, 9β,15β-bisdeuterio9α,11α,15α-trihydroxy-5-cis, 13-trans-prostadienoic acid was found to have smooth muscle stimulating activity.

The compounds of the instant invention are conveniently prepared by contacting a compound of the formula

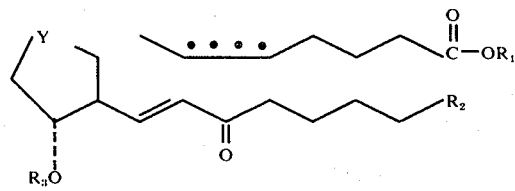

wherein Y is a keto, or β-hydroxymethylene radical; $R_3$ is a tetrahydropyran-2-yl, 4-alkoxytetrahydropyran-4-yl or trialkylsilyl radical; and $R_1$ and $R_2$ are defined as hereinabove; with a suitable deuterated reducing agent. This reaction is preferably conducted in an inert solvent. Suitable solvents include methylene chloride, 1-deuteroxy2,2,2-trifluoroethane, ethyl ether, and tetrahydrofuran. A particularly preferred solvent is tetrahydrofuran. Deuterated reducing agents which are particularly useful in the instant process are sodium borodeuteride, sodium cyanoborodeuteride and lithium perhydro-9b-boraphenalyldeuteride. Other useful reducing reagents for this purpose are the trialkylborodeuterides.

Reaction conditions such as time, temperature and pressure are not critical but generally depend on the particular deuterated reducing agent that is used.

An alternate route for the production of the instant compounds wherein X is oxo involves oxidation of a compound of the formula

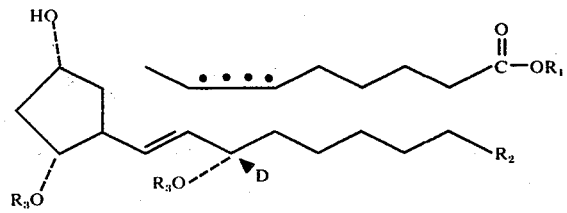

wherein $R_1$, $R_2$ and $R_3$ are defined as before, followed by contact with a proton donor to obtain the free dihydroxy compound.

This reaction may or may not be conducted in a solvent, although the use of a solvent is generally preferred. A particularly suitable oxidizing agent is Collins reagent. Time, temperature and pressure are not critical for the conduct of the reaction.

The starting materials of the instant invention are conveniently prepared by oxidation of the corresponding 15-hydroxy compound to give the required 15-oxo starting materials and protection of the remaining α-hydroxy groups. A preferred oxidizing reagent for this purpose is dichlorodicyanobenzoquinone, or activated manganese dioxide.

Suitable protecting reagents include, but are not limited to, dihydro-γ-pyran, 4-alkoxy-2,3-dihydro-α-pyrans, trialkylsilyl halides or trialkylsilyldiethylamines. The protecting reaction is conveniently carried out in a solvent such as methylene chloride, tetrahydrofuran, and pyridine. Preferably a catalytic amount of p-toluenesulfonic acid is added to the reaction mixture to promote the formation of the pyranyl ethers. Also, when trialkylsilyl ethers are formed using tetrahydrofuran as the solvent, it is desirable to add the corresponding hexaalkyldisilazane to the solvent to improve the yield.

The following examples describe in detail compounds illustrative of the present invention and methods which have been devised for their preparation. It will be apparent to those skilled in the art that many modifications, both of materials and method, may be practiced without departing from the purpose and intent of this disclosure. Throughout these examples, temperatures are given in degrees centigrade (° C.) and relative amounts of materials in parts by weight, unless otherwise noted.

EXAMPLE 1

A suspension of 2.0 parts of lithium deuteride and 394 parts of 9-borabicyclo[3.3.1]nonane in 267 parts of freshly distilled tetrahydrofuran is refluxed under a nitrogen atmosphere for 2 hours. The solution is filtered to remove insoluble material. The resulting 205 ml. of filtrate is 1.09 N lithium perhydro-9b-boraphenalyldeuteride in tetrahydrofuran.

EXAMPLE 2

To a solution of 0.51 part of 9,15-dioxo-11α-(tetrahydropyran-2'-yl)oxy-13-trans-prostenoic acid in 62 parts of tetrahydrofuran is added 2.4 parts by volume of a 1.09 N solution of lithium perhydro-9b-boraphenalyldeuteride in tetrahydrofuran in a Dry Ice-acetone bath under a nitrogen atmosphere. The resulting solution is stirred at −78° C. for two hours, poured into a cold aqueous citric acid solution and the citric acid solution extracted with ethyl ether. The ethereal extracts are washed with a 1% sodium chloride solution, dried over sodium sulfate, concentrated and chromatographed on 70 parts of silicic acid. The elution is started with a 95:5 benzene-ethyl acetate mixture and continued with increasing amounts of ethyl acetate. The 20–60% ethyl acetate fractions give crude 15β-deuterio-15α-hydroxy-9-oxo-11α-(tetrahydropyran-2'-yl)-13-trans-prostenoic acid and crude 9β,15β-deuterio-9α,15α-dihydroxy-11α-(tetrahydropyran-2'-yl)-13-trans-prostenoic acid. The 100% ethyl acetate fractions give crude 15β-deuterio-11α,15α-dihydroxy-9-oxo-13-trans-prostenoic acid followed by crude 9β,15β-bisdeuterio-9α,11α,15α-trihydroxy-13-trans-prostenoic acid.

The fraction containing the crude tetrahydropyran-2'-yl ethers is dissolved in 100 parts by volume of a 20:10:3 mixture of acetic acid-water-tetrahydrofuran and kept at room temperature for 24 hours. It is then chromatographed on 50 parts of silicic acid. The 75:25 ethyl acetate-benzene fraction yields 15β-deuterio-11α,15α-dihydroxy-9-oxo-13-trans-prostenoic acid, while the 100% ethyl acetate yields 9β,15β-bisdeuterio-9α,11α,15α-trihydroxy-13-trans-prostenoic acid.

The pure 15β-deuterio-11α,15α-dihydroxy-9-oxo-13-trans-prostenoic acid is obtained by partition chromatography [Miyano, Dorn and Mueller, *J. Org. Chem.*, 37, 1810 (1972)] on 15 parts of silicic acid and recrystallization from ethyl acetate. This product melts at 114° C. and is represented by the following structural formula

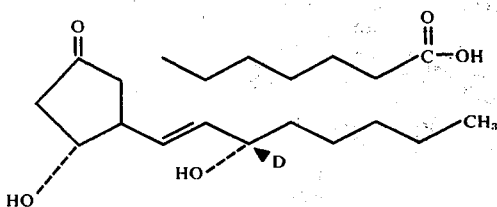

Pure 9β,15β-bisdeuterio-9α,11α,15α-trihydroxy-13-trans-prostenoic acid is obtained by recrystallization from ethyl ether to give a product melting at 89.5° C. and represented by the following structure

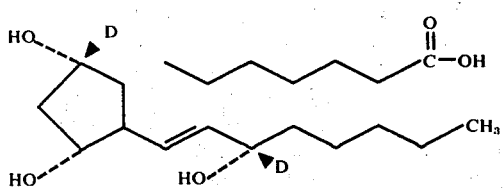

EXAMPLE 3

A solution of 0.9 part of 9,15-dioxo-20-methyl-11α-(tetrahydropyran-2′-yl)oxy-13-trans-prostenoic acid in 45 parts of tetrahydrofuran is treated with 10 parts by volume of a 1.09 N solution of lithium perhydro-9b-boraphenalyldeuteride in tetrahydrofuran in a Dry Ice-acetone bath under a nitrogen atmosphere for three hours. The reaction mixture is then poured into a cold aqueous citric acid solution and extracted with ethyl ether. The ethereal extract is washed with a 1% sodium hydroxide solution. The aqueous alkaline phase is acidified with citric acid and extracted with ethyl ether. The ethereal extract is washed with a 10% sodium chloride solution, dried over sodium sulfate, concentrated and chromatographed on 70 parts of silicic acid. The elution is begun using 30:70 ethyl acetate-benzene solutions and carried on with increasing amounts of ethyl acetate. The desired material, 9β,15β-bisdeuterio-20-methyl-9α,11α,15α-trihydroxy-13-trans-prostenoic acid, is found in the 100% ethyl acetate fractions. This crude material is recrystallized from ethyl acetate to give a product melting at about 101° C. and which is represented by the following structural formula

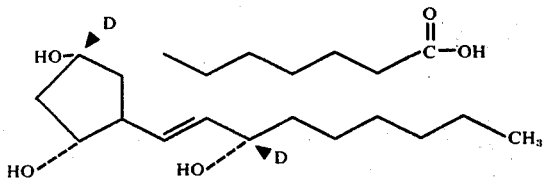

EXAMPLE 4

1.0 Part of natural PGE₂ (11α,15α-dihydroxy-9-oxo-5-cis,13-trans-prostadienoic acid) is oxidized by treatment with 4.0 parts of dichlorodicyanobenzoquinone in 40 parts of dioxane at room temperature for 48 hours. The desired product 9,15-dioxo-11α-hydroxy-5-cis,13-trans-prostadienoic acid, is eluted from a silicic acid column with a 20:80 ethyl acetate-benzene solution and crystallizes upon standing.

A solution of 3.53 parts of 9,15-dioxo-11α-hydroxy-5-cis,13-trans-prostadienoic acid, 3.40 parts of imidazole and 3.62 parts of dimethyl-t-butylchlorosilane in 9.5 parts of N,N-dimethylformamide is left standing at room temperature for 96 hours. The reaction mixture is then poured into an aqueous citric acid solution and extracted with ethyl ether. The ethereal extract is washed with a 1% sodium chloride solution, dried over sodium sulfate, and concentrated to yield crude 11α-(dimethyl-t-butylsilyl)oxy-9,15-dioxo-5-cis, 13-trans-prostadienoic acid.

When 5.2 parts of 11α-(dimethyl-t-butylsilyl) oxy-9,15-dioxo-5-cis,13-trans-prostadienoic acid is substituted for 9,15-dioxo-20-methyl-11α-(tetrahydropyran-2′-yl)oxy-13-trans-prostenoic acid of Example 3 and the procedure therein substantially repeated, there is obtained 9β,15β-bisdeuterio-9α,11α,15α-trihydroxy-5-cis,13-trans-prostadienoic acid. The crude product is chromatographed on silicic acid to give a product melting at about 25° C. and represented by the following structural formula

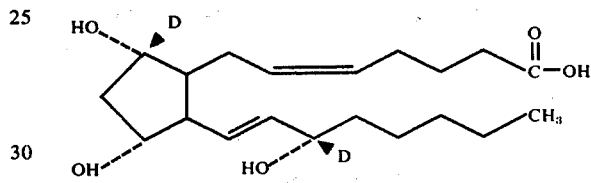

EXAMPLE 5

An equivolume mixture of trifluoroethanol and deuterated water is combined and distilled three times using a one-foot rectifying column to give 1-dueteroxy-2,2,2-trifluoroethane. This deuterated alcohol boils at 73°–75° C.

A solution of 1.0 part of 9,15-dioxo-11α-hydroxy-5-cis,13-trans-prostadienoic acid and 0.7 part of sodium cyanoborodeuteride [Borch, Bernstein and Durst, J. Am. Chem. Soc., 93, 2897 (1971)] in 50 parts by volume of 1-deuteroxy-2,2,2-trifluoroethane is allowed to stand for 96 hours. The reaction mixture is then heated to 50°–55° C. for 12 days. This mixture is poured into a 1% aqueous solution of citric acid and extracted with ethyl ether. The ethereal extracts are then washed with a 1% sodium chloride solution, dried over sodium sulfate, concentrated and chromatographed on 40 parts of silicic acid. The elution is started with a 50:50 ethyl acetate-benzene solution and continued with progressively higher ratios of ethyl acetate. The desired 15β-deuterio-11α,15α-dihydroxy-9-oxo-5-cis,13-trans-prostadienoic acid is isolated from the 75:25 ethyl acetate-benzene fractions. This product is indistinguishable from natural PGE₂ on thin-layer chromatography plates.

It was established by the mass spectrum of the methoxime tris(trimethysilyl) derivative that the present compound contains an additional deuterium atom.

EXAMPLE 6

A solution of 0.55 part of 9β,11α,15α-trihydroxy-5-cis,13-trans-prostadienoic acid and 2.0 parts of dichlorodicyanobenzoquinone in 206 parts of dioxane is allowed to stand for 96 hours. The reaction mixture is concentrated in vacuo and chromatographed on 260 parts of silicic acid. The desired product, 9β,11α-dihydroxy-15-oxo-5-cis,13-trans-prostadienoic acid is eluted with a 70:30 ethyl acetatebenzene solution.

0.37 part of 9β,11α-dihydroxy-15-oxo-5-cis,13-trans-prostadienoic acid is dissolved in 80 parts of methanol and contacted with 2.0 parts of sodium borodeuteride at a temperature of 0°-20°C. The reaction mixture is diluted with water, acidified with citric acid, and extracted with 3 portions of ethyl ether. The ethereal extracts are combined, washed with 1% sodium chloride, dried over anhydrous sodium sulfate, concentrated, and chromatographed on silicic acid. The desired product, 15β-deuterio - 9β, 11α, 15α - trihydroxy - 5 - cis, 13 - trans - prostadienoic acid, is eluted with 100% ethyl acetate and recrystallized from ethyl ether. The recrystallized product melts at 96°-97°C. This product is represented by the following structural formula

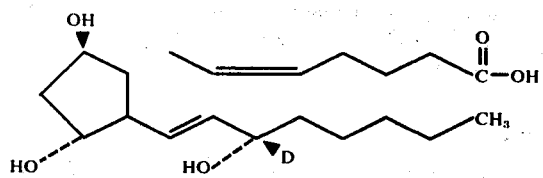

EXAMPLE 7

When the 9,15-dioxo-11α-(tetrahydropyran-2'-yl)oxy-13-trans-prostenoic acid of Example 2 is replaced with an equivalent quantity of 11α-dimethyl-t-butylsilyl)oxy-9,15-dioxo-5-cis,13-trans-prostadienoic acid and the procedure of Example 2 substantially repeated, there is obtained 9β,15β-bisdeuterio-9α,11α,15α-trihydroxy-5-cis,13-trans-prostadienoic acid and 15β-deuterio - 9 - oxo - 11α, 15α - dihydroxy - 5 - cis, 13 - trans-prostadienoic acid. The latter is recrystallized from a mixture of ethyl acetate and n-pentane to give a product melting at 68°C. and displaying an [α]$_D$ = —66°[C = 1.0 in tetrahydrofuran]. This product is represented by the following structural formula

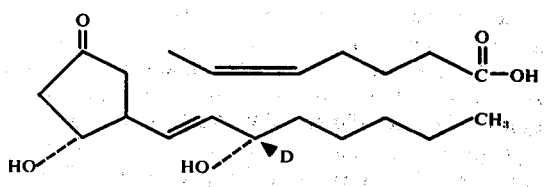

EXAMPLE 8

Substitution of an equivalent amount of natural PGF$_2$ (9α, 11α, 15α - trihydroxy - 5 - cis, 13 - trans - prostadienoic acid) for the 9β,11α,15α-trihydroxy-5-cis,13-trans-prostadienoic acid of Example 6 and substantial repetition of the procedure described therein gives 15β-deuterio-9α,11α,15α-trihydroxy-5-cis, 13-trans-prostadienoic acid, melting at approximately 30°C. and represented by the following structural formula

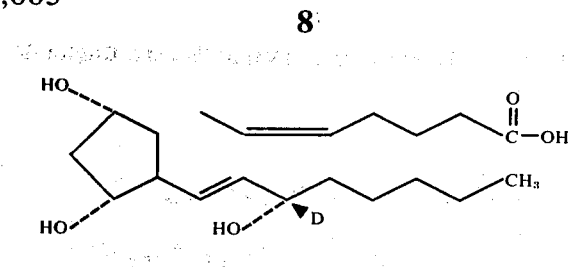

EXAMPLE 9

To a solution of 0.34 part of 9β,15β-bisdeuterio-9α,11α,15α-trihydroxy-5-cis,13-trans-prostadienoic acid in 2.4 parts of acetone is added 0.56 part of trimethylsilyl diethylamine in a Dry Ice-acetone bath. The mixture is stirred at —45° to —40° C. for 2 hours. The cold reaction mixture is then added to a suspension of Collins reagent (prepared from 1.2 parts of chromic trioxide and 1.9 parts of pyridine and 79 parts of methylene chloride) and stirred for 10 minutes. The mixture is filtered through 30 parts of silicic acid. The filtrate is then shaken with 2% aqueous citric acid and ethyl ether. The ethereal extract is washed with water, concentrated and the residue is dissolved in 10 parts by volume of a 20:10:3 acetic acid-water-tetrahydrofuran mixture. After 10 minutes the acid solvent is removed, and the residue chromatographed on 30 parts of silicic acid. A 50:50 solution of ethyl acetate-benzene is used to elute the desired 15β-deuterio-11α-hydroxy-9-oxo-5-cis,13-trans-prostadienoic acid. This product, recrystallized from ethyl acetate, melts at about 68.5° C. and is represented by the following structural formula

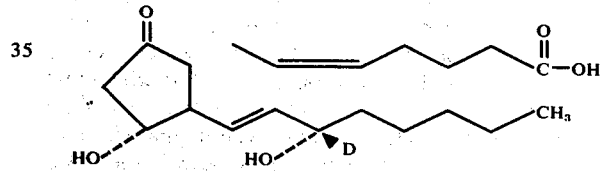

EXAMPLE 10

When an equivalent quantity of 9,15-dioxo-11α-(tetrahydropyran-2'-yl)oxy-5-cis,13-trans-prostadienoic acid methyl ester is substituted for the 9,15-dioxo-20-methyl-11α-(tetrahydropyran-2'-yl)oxy-13-trans-prostenoic acid of Example 3, and the procedure therein substantially repeated, there is obtained 9β,15β-bisdeuterio-9α,11α,15α-trihydroxy-5-cis,13-trans-prostadienoic acid methyl ester. This compound is represented by the following structural formula

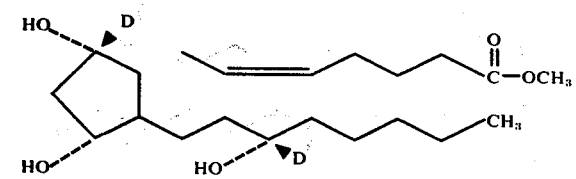

What is claimed is:
1. A compound which is 9β,15β-bisdeuterio-9α,1-1α,15α-trihydroxy-5-cis,13-trans-prostadienoic acid methyl ester.
2. A compound which is 9β,15β-bisdeuterio-9α,1-1α,15α-trihydroxy-5-cis,13-trans-prostadienoic acid.
3. A compound which is 15β-deuterio-9β,11α,15α-trihydroxy-5-cis,13-trans-prostadienoic acid.

* * * * *

UNITED STATES PATENT AND TRADEMARK OFFICE
CERTIFICATE OF CORRECTION

PATENT NO. : 4,002,663
DATED : Jan. 11, 1977
INVENTOR(S) : Masateru Miyano

It is certified that error appears in the above—identified patent and that said Letters Patent are hereby corrected as shown below:

Column 6, line 37, "dueteroxy" should read -- deuteroxy --.

All formulas except Example 4 formula, in part,

" 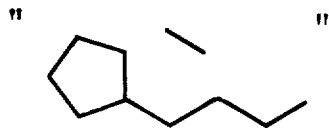 "     should read     -- 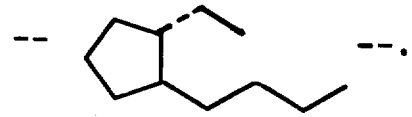 --.

Signed and Sealed this

Twenty-eighth Day of June 1977

[SEAL]

Attest:

RUTH C. MASON
*Attesting Officer*

C. MARSHALL DANN
*Commissioner of Patents and Trademarks*